United States Patent
Lippert et al.

(10) Patent No.: US 8,271,085 B2
(45) Date of Patent: Sep. 18, 2012

(54) IMPLANTABLE MEDICAL DEVICE FOR BLOOD CONDUCTIVITY, BLOOD IMPEDANCE, AND/OR HEMATOCRIT MEASUREMENT

(75) Inventors: Michael Lippert, Ansbach (DE); Olaf Skerl, Bad Doberan (DE); Stefan Paule, Drosendorf (DE); Bernhard Fahn, Nürnberg (DE); Gerald Czygan, Buckenhof (DE); Heinrich Reinke, Fürth (DE); Albrecht Urbaszek, Heroldsbach (DE)

(73) Assignee: Biotronik CRM Patent AG (CH)

( * ) Notice: Subject to any disclaimer, the term of this patent is extended or adjusted under 35 U.S.C. 154(b) by 1042 days.

(21) Appl. No.: 11/970,662

(22) Filed: Jan. 8, 2008

(65) Prior Publication Data
US 2008/0195162 A1     Aug. 14, 2008

(30) Foreign Application Priority Data

Feb. 8, 2007   (DE) .......................... 10 2007 006 229

(51) Int. Cl.
*A61N 1/365*    (2006.01)
(52) U.S. Cl. ............................................. 607/18; 607/2
(58) Field of Classification Search .................. 607/2, 4, 607/9, 17, 18; 600/508, 509, 513
See application file for complete search history.

(56) References Cited

U.S. PATENT DOCUMENTS

| | | | | |
|---|---|---|---|---|
| RE30,007 E | * | 5/1979 | Steuer et al. | 324/30 |
| 4,676,252 A | | 6/1987 | Trautman et al. | |
| 5,526,808 A | * | 6/1996 | Kaminsky | 600/370 |
| 7,395,114 B2 | * | 7/2008 | Czygan et al. | 607/6 |
| 2006/0025661 A1 | | 2/2006 | Sweeney et al. | |
| 2006/0041280 A1 | | 2/2006 | Stahmann et al. | |
| 2006/0293609 A1 | | 12/2006 | Stahmann et al. | |

FOREIGN PATENT DOCUMENTS

| | | |
|---|---|---|
| EP | 1 825 807 A2 | 8/2007 |
| WO | WO 01/88521 A1 | 11/2001 |
| WO | WO 2006/017446 A1 | 2/2006 |

OTHER PUBLICATIONS

Wei, C., et al, "Evidence of Time Varying Myocardial Contribution by In Vivo Magnitude and Phase Measurement in Mice," *Proceedings of the 26th Annual International Conference of the IEEE EMBS*, Sep. 1-5, 2004, pp. 3674-3677, Fig. 4, San Francisco, CA, USA.

(Continued)

*Primary Examiner* — Carl H Layno
*Assistant Examiner* — Brian T Gedeon
(74) *Attorney, Agent, or Firm* — Craig A. Fieschko, Esp.; DeWitt Ross & Stevens S.C.

(57) ABSTRACT

An implantable medical device has an impedance or admittance determination unit, an alternating current or voltage source, a measuring unit, and an analysis unit which is connected to the alternating current or AC voltage source and the measuring unit to calculate an impedance value or an admittance value at different times. The impedance or admittance determination unit may generate measuring current having two different frequencies (preferably below 100 kHz), and the analysis unit may calculate pairs of impedance or admittance values which are chronologically assigned to one another for different frequencies of the measuring current, and calculate a value for a blood impedance or blood admittance component which is independent of the impedance of the body tissue surrounding a particular blood vessel, The analysis unit may also determine trends in this value over time as an indicator for a change of blood hematocrit value.

23 Claims, 3 Drawing Sheets

OTHER PUBLICATIONS

Guyader, P., et al., "Myocardial Impedance Measurements with a Modified Four Electrode Technique," *Engineering in Medicine and Biology Society*, 1994; *Engineering Advances: New Opportunities for Biomedical Engineers, Proceedings of the 16$^{th}$ Annual International Conference of the IEEE*, Nov. 3-6, 1994, vol. 2, pp. 880-881, Fig. 1.

* cited by examiner

FIG. 3 ial cardiac pacemakers or implantable cardioverters/defibrillators or a combination of both, which are implemented to detect values accompanying changes of the hematocrit value of blood.

IMPLANTABLE MEDICAL DEVICE FOR BLOOD CONDUCTIVITY, BLOOD IMPEDANCE, AND/OR HEMATOCRIT MEASUREMENT

FIELD OF THE INVENTION

The present invention relates to an implantable medical device having means for determining values which reflect a change of a hematocrit value of blood in a characteristic way. In particular, the present invention relates to implantable cardiac pacemakers or implantable cardioverters/defibrillators or a combination of both, which are implemented to detect values accompanying changes of the hematocrit value of blood.

BACKGROUND OF THE INVENTION

Cardiac pacemakers which are implemented for the purpose of estimating a hematocrit value on the basis of a blood conductivity measurement or blood impedance measurement are known from the prior art, for example, from WO 2006/017446.

The device known from WO 2006/017446 uses the fact that the electrical conductivity of the blood is primarily a function of the particular hematocrit value.

The hematocrit value (HCT) refers to the volume proportion of cellular components and is a measure of the viscosity of the blood.

In addition, the hematocrit value is an important physiological variable whose observation permits conclusions about the pathophysiological state of a particular patient. In particular, changes of the particular hematocrit value are of interest here. The observation of the change of a particular hematocrit value may be used for the purpose of optimizing a particular medication treatment.

Typical methods known from the prior art for determining the hematocrit value are based on centrifuging, counting the erythrocytes, optical methods, or impedance measurement.

In addition, a particular known hematocrit value may be used as a correction value when determining the thorax impedance, as is known from US 2006/0041280.

SUMMARY OF THE INVENTION

The present invention is based on the object of providing an implantable medical device which provides values which indicate a change of the particular hematocrit value, and which are as reliable as possible. A determination of the absolute hematocrit value is therefore not the focus. Rather, the relative change of the hematocrit value is of interest. This is based on the finding that in particular the change of the particular hematocrit value is of interest.

According to the present invention, this object is achieved by an implantable medical device which has an impedance or admittance determination unit, which is connected or is to be connected to electrodes to be placed intracardially or intraluminally to deliver a measuring current. In addition, the implantable medical device has an alternating current or AC voltage source, which is implemented to generate the measuring current as alternating current having constant current amplitude or as AC voltage having constant voltage amplitude, and to feed it into the body of the patient in operation via the electrode connected to the alternating current or AC voltage source. A further component of the implantable medical device according to the present invention is a measuring unit which is implemented to detect a voltage drop caused as a result of the fed constant measuring current between two of the electrodes or the current strength of the measuring current fed at constant voltage in operation. A further component of the implantable medical device according to the present invention is an analysis unit which is connected to the alternating current or AC voltage source and the measuring unit and is implemented to calculate an impedance value or an admittance value for various instants from the constant current amplitude of the particular fed measuring current and the voltage drop measured as a result thereof or the particular constant voltage amplitude of the fed measuring voltage and the current strength of the measuring current resulting therefrom. The impedance or admittance determination unit is further implemented for the purpose of generating measuring currents at two different frequencies below 500 kHz and preferably below 200 kHz and/or 100 kHz. The analysis unit is further implemented for the purpose of calculating pairs of two impedance or admittance values assigned to one another in time for different frequencies of the measuring current from a particular pair of impedance values of a value for a blood impedance or blood admittance component which is as independent as possible from the impedance of the body tissue surrounding a particular blood vessel, to then be able to determine a relative change of this value over time as an indicator for a change of a hematocrit value of the blood from values of the blood impedance or blood admittance component determined for various instants.

The admittance, which is to be determined alternatively to the impedance, is the reciprocal of the impedance and thus a blood conductivity value dependent on the frequency of a particular alternating current.

The present invention is based on the finding that the determination of a blood impedance trend or blood admittance trend characteristic for a change of a particular hematocrit value is made more difficult in that the blood conductivity (blood admittance) and correspondingly also the blood impedance are not only a function of the particular hematocrit value, but rather also of the blood temperature. In addition, the particular geometry of the electrodes used for the impedance measurement and their position in relation to the body tissue play a role. The latter may change in the course of time. Furthermore, not only the particular blood impedance (and/or blood admittance) is incorporated in every intraluminal or intracardial blood impedance measurement (i.e., in every intracorporeal blood impedance measurement), but rather also the impedance and/or admittance of the surrounding tissue.

The blood impedance is approximately constant in a frequency range between 1 kHz and 100 kHz, while the impedance of the body tissue, in particular the impedance of the myocardium (muscle tissue of the heart) is a function of the frequency of the particular measuring current in a way known from the literature. For example, the conductivity and thus the impedance of the myocardium changes by a factor of 1.48 between 2 kHz and 20 kHz.

Because the current path through the blood and the current path through the tissue are to be viewed as parallel current paths, it results that the total admittance Y(f) is at least approximately to be described by the following formula:

$$Y(f) = c \cdot [(1-a) \cdot \sigma_{blood} + a \cdot \sigma_{myocardium}(f)]$$

in which
$\sigma_{blood}$ is the specific conductivity of the blood,
$\sigma_{myocardium}$ is the specific conductivity of the myocardium,
f is the frequency of the measuring current,
c is an (approximately constant) factor which is a function of the electrode geometry, and a is the unknown component of the myocardial impedance (and/or myocardial admittance) of the total admittance, which is a function of how myocardium and blood are distributed in proximity to the measuring electrodes. For example, a increases when the measuring electrodes move closer to a particular cardiac wall.

If the impedance is measured at two different frequencies, the unknown factor a may be determined and the blood conductivity (blood admittance) may be isolated from the total admittance, in that the component of the myocardial admittance of the total impedance is determined with the aid of the factor a. This factor a changes, for example, due to the movement of the heart, respiration, position changes of the patient, but also in the long term by changes of the electrode geometry as a result of slipping or ingrowth into the cardiac tissue.

In view of the above statements, the analysis unit is preferably implemented to analyze two admittance values recorded at different frequencies of the measuring current (which each form a pair) on the basis of the above formula in such a way that the factor a is determined. In this way, the trend of the change of the blood conductivity value may be filtered from the influence of the tissue impedance.

The implantable medical device is preferably implemented for the purpose of changing the electrode configuration for determining the blood admittance component or the blood impedance component from time to time, for example, from measurement to measurement. For this purpose, the implantable medical device preferably has appropriate switches, such as a switching matrix in the form of a semiconductor, which changes over the alternating current or AC voltage source and the measuring unit between various electrodes and/or the terminals for various electrodes.

By changing the electrode configurations, the influence of the tissue impedance on the total impedance may also be determined, without measurements using measuring currents of different frequencies being necessary for this purpose. The changing of the measuring electrode configurations thus also represents an idea of the present invention to be implemented independently, which increases the precision of the determination of the blood impedance in connection with measurements at various frequencies.

Suitable electrode configurations are as follows:

In an especially advantageous quadropolar impedance or admittance measurement, the current is fed via a housing electrode of the implant and a right-ventricular tip electrode. The voltage is measured via a ventricular shock coil and a right-ventricular ring electrode. The housing electrode is formed by an electrically conductive part of a housing of the implantable medical device. The shock coil is a ventricular defibrillation electrode, as is provided on corresponding electrode lines.

In addition to these quadropolar electrode configurations, an array of tripolar configurations also come into consideration, which are shown in the following overview. I indicates the electrode pair via which the current is fed, while U identifies the electrode pair via which the particular voltage measurement occurs:
I: ventricular shock coil—right-ventricular tip electrode,
U: ventricular shock coil—right-ventricular ring electrode;
I: ventricular shock coil—right-ventricular ring electrode
U: ventricular shock coil—right-ventricular tip electrode;
I: ventricular shock coil—housing electrode,
U: ventricular shock coil—right-ventricular tip electrode;
I: ventricular shock coil—housing electrode,
U: ventricular shock coil—right-ventricular ring electrode.

In these tripolar electrode configurations, the ventricular shock coil is advantageously thus used as a joint electrode for the current feed and the voltage measurement.

For the case in which the implantable medical device is not connected to an electrode line for delivering ventricular defibrillation shocks, so that the electrode line does not have a ventricular shock coil, the following configurations come into consideration:
I: right-ventricular ring electrode—housing electrode,
U: right-ventricular ring electrode—right-ventricular tip electrode;
I: right-ventricular ring electrode—right-atrial ring electrode,
U: right-ventricular ring electrode—right-ventricular tip electrode;
I: right-atrial ring electrode—housing electrode,
U: right-atrial ring electrode—right-atrial tip electrode;
I: right-atrial ring electrode—right-ventricular ring electrode,
U: right-atrial ring electrode—right-atrial tip electrode.

The bipolar electrode configurations cited in the following have the disadvantage that the proportion of the myocardial impedance of the total impedance is greater than in the above-mentioned electrode configurations, because the particular tip electrode has a greater proximity to the heart wall. The following bipolar configurations nonetheless also fundamentally come into consideration.
I: right-ventricular tip electrode—right-ventricular ring electrode,
U: right-ventricular tip electrode—right-ventricular ring electrode
I: right-atrial tip electrode—right-atrial ring electrode,
U: right-atrial tip electrode—right-atrial ring electrode.

Configurations in which the housing electrode forms a shared electrode are to be avoided if possible, because the impedance of the tissue surrounding the implantable medical device and the lung impedance then have an unnecessarily great influence on the measurement result.

The analysis unit is—as already indicated above—preferably implemented in such a way that it calculates pairs of associated impedance values for various instants and two different frequencies of the measuring current in each case from the constant current strength of the particular fed measuring current and the voltage drop measured as a result thereof. The two associated impedance values are preferably calculated simultaneously and/or quasi-simultaneously, i.e., immediately one after another, so that a negligible time interval exists between them in any case. The particular measuring current having constant current strength but different frequencies is preferably delivered in the form of two-phase current pulses. The voltage drop is measured so that the impedance may then simply be determined.

It is preferable if the analysis unit for determining the relative change of the value of the blood impedance component over time (i.e., for determining the trend of the blood impedance) does not consider all recorded pairs of associated impedance values, but rather only considers those pairs of impedance values in a particular time window or within a particular sequence of pairs which represent the lowest impedance values. For example, the analysis unit may be implemented to calculate the quartile which represents the lowest impedance values for a particular time window or for a particular sequence of pairs of impedance values. A quartile contains a fourth of the pairs of impedance values, sorted by size, for a particular time window and/or a particular sequence. After determining the lowest quartile of pairs of impedance values, the pairs of impedance values can be averaged over this quartile. The background is that short-term changes of the impedance values as a result of the heart movement or respiration, for example, result in the lowest impedance values of a sequence of impedance values each being attributed most strongly to the blood impedance and being influenced least by the tissue impedance, because the impedance of the blood is lower than the impedance of the surrounding tissue. Accordingly, the lowest impedance values within a time window or a sequence of impedance values are those impedance values which are influenced least by movement artifacts.

In addition, it may be advantageous if the analysis unit is implemented to eliminate short-term changes of the impedance values by averaging the signal over various time windows.

As already noted above, the blood conductivity and/or the resistance of the blood (the impedance) is not only a function of the hematocrit value, but rather also the blood temperature. For blood having a hematocrit value in the range between 16% and 52.5%, the specific blood resistance ρ for a measuring current having a frequency of 100 kHz within a temperature range between 22° C. and 40° C. is a function of the blood temperature and the hematocrit value as follows:

$$\rho = [(627.2 \cdot HTC + 75.176) - (10.4 \cdot HTC + 1.467) \cdot T]$$

in which the temperature T in ° C. is to be used and the specific resistance has the unit Ωcm. To be able to cancel out the influence of the body temperature and thus the blood temperature when determining the trend of the blood impedance change and thus be able to isolate the influence of the hematocrit value, the implantable medical device preferably has a temperature determination unit, which is to be connected to a temperature sensor in an electrode line and implemented to determine blood temperature changes. The temperature determination unit is connected to the analysis unit and the analysis unit is in turn implemented to consider changes of the blood temperature when determining the relative change of the value of the blood impedance and the blood admittance component over time. The temperature sensor is preferably housed in proximity to the electrodes, via which the voltage is measured, for example.

In addition, the implantable medical device preferably has a memory for relative blood impedance values determined by the analysis unit. In this way, multiple blood impedance values may be stored and the trend of their change may be detected. A memory is preferably connected to a telemetry unit for wireless transmission of relative blood impedance values. In this way, these blood impedance values may be transmitted to a central service center, for example, and collected accordingly there and also analyzed over longer periods of time.

In this context, it is advantageous if the analysis unit is implemented to determine the amplitude of a circadian oscillation of the measured impedance values. An analysis unit which is implemented to detect the changes of the amplitude of a circadian oscillation of the measured impedance values as indicators for changes of the hematocrit value is especially preferred.

The implantable medical device is preferably in implantable cardiac pacemaker or an implantable cardioverter/defibrillator or a combination of both. In operation, these devices are typically connected to electrode lines which in turn typically have the above-mentioned electrodes.

The implantable medical device is preferably implemented for the purpose of transmitting blood impedance values measured in the meantime to an external device at regular intervals, for example, at intervals of 24 hours.

In addition, either the implantable medical device, especially its analysis unit, or an external device, which receives and analyzes the telemetrically transmitted blood impedance values, may be implemented in such a way that the device generates an automatic alarm if the blood impedance or the blood conductivity changes suddenly or rapidly.

In addition, either the implantable device itself or an external device, which receives the blood impedance values, may be implemented to detect the oscillations of the blood impedance or blood conductivity in the course of a circadian rhythm. A regression of the hematocrit value is typically also connected to a regression of the oscillation amplitude of the blood impedance or the blood conductivity value. Because the circadian rhythm (daily rhythm) has a relatively long-lasting period, the detection of the amplitude of the blood impedance of the blood conductivity change in the circadian rhythm is less susceptible to interference.

Furthermore, the implantable medical device itself or an external device may be implemented for the purpose of providing correction values for other impedance measurements, for example, the measurement of the lung impedance or for the impedance plethysmography, from a change of the blood impedance originating from a change of the hematocrit value. For example, impedance measurements are performed to detect changes of the heart geometry or the lung geometry or the conductivity of the lung tissue. Impedance measurements via impedance plethysmography are also used for determining the volume changes of the left ventricle, or for determining the liquid content of the lungs, or for determining the respiration rate, or for determining the respiration volume, or for determining the right-ventricular apical contraction dynamics. All of these measurements may be corrected in regard to change of the blood conductivity as a result of a changing hematocrit value if a change of the hematocrit value is detected using an implantable medical device of the type according to the present invention.

A further application of the implantable medical device according to the present invention comprises detecting a thrombus in the right or left atrium as a result of atrial flutter. The formation of a thrombus changes the local conductivity of the blood and may also be detected by analyzing the blood impedance in the atrium. In particular an impedance measurement via atrial electrodes comes into consideration here, for example, both current supply and also voltage measurement via the right atrial tip electrode and the right atrial ring electrode.

It is intended that the various aspects described here and set forth as subelements of the claims may be combined with one another, if they are not mutually exclusive.

BRIEF DESCRIPTION OF THE DRAWINGS

The present invention will be explained in greater detail on the basis of exemplary embodiments with reference to the figures.

In the figures.

DETAILED DESCRIPTION

Figure 1:
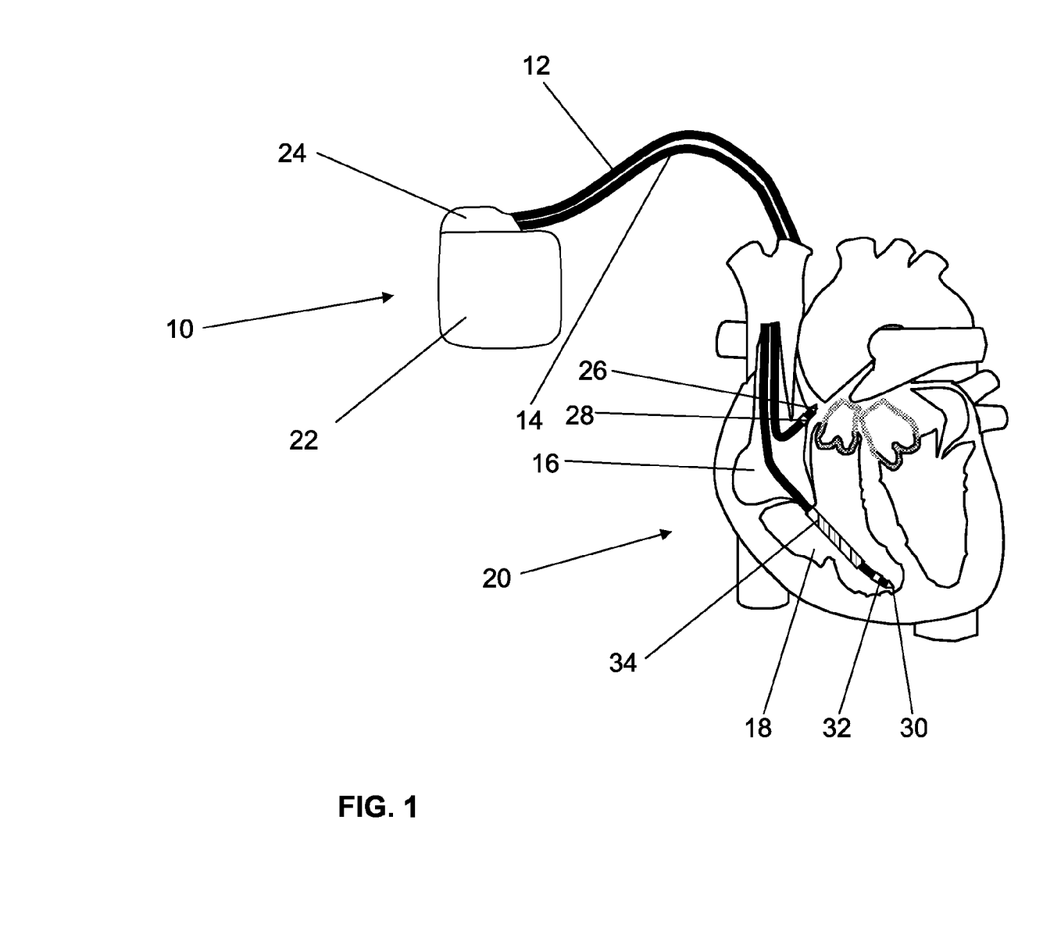
FIG. 1: shows an implantable cardiac pacemaker/defibrillator having electrode lines connected thereto and their placement in the heart of a human.

FIG. 1 shows how an implantable medical device 10, in this case a cardiac pacemaker/defibrillator, is connected via electrode lines 12 and 14 to various electrodes, which are situated in an atrium 16 and a ventricle 18 of a heart 20.

The electrode lines 12 and 14 are connected at their particular proximal end using a plug contact to electronics in the interior of a housing 22 of the cardiac pacemaker 10. The housing 22 of the cardiac pacemaker 10 is hermetically sealed and comprises a conductive, biocompatible material, for example, titanium. A so-called header 24 is fastened to the housing 22, which is typically made of transparent plastic and has sockets for receiving the plugs on the particular proximal ends of the electrode lines 12 and 14. These sockets have electrical contacts (not shown in greater detail), which are electrically connected via a feed through to the electronics in the interior of the housing 22 of the cardiac pacemaker 10.

Of the two electrode lines 12 and 14, one electrode line is a right-atrial electrode line 12. It carries a right-atrial tip electrode 26 on its distal end and a right-atrial ring electrode 28 at a small distance therefrom. The right-atrial tip electrode 26 and the right-atrial ring electrode 28 are located in the atrium 16 of the heart 20 in the implanted state of the atrial electrode line 12.

The other electrode line is a right-ventricular electrode line 14. This carries a right-ventricular tip electrode 30 on its distal end and a right-ventricular ring electrode 32 at a small distance therefrom. In addition, a ventricular shock coil 34, which forms a large-area electrode for delivering defibrillation shocks and is typically implemented as coiled in a helix for the sake of mobility, is situated on the right-ventricular electrode line 14.

Figure 2:
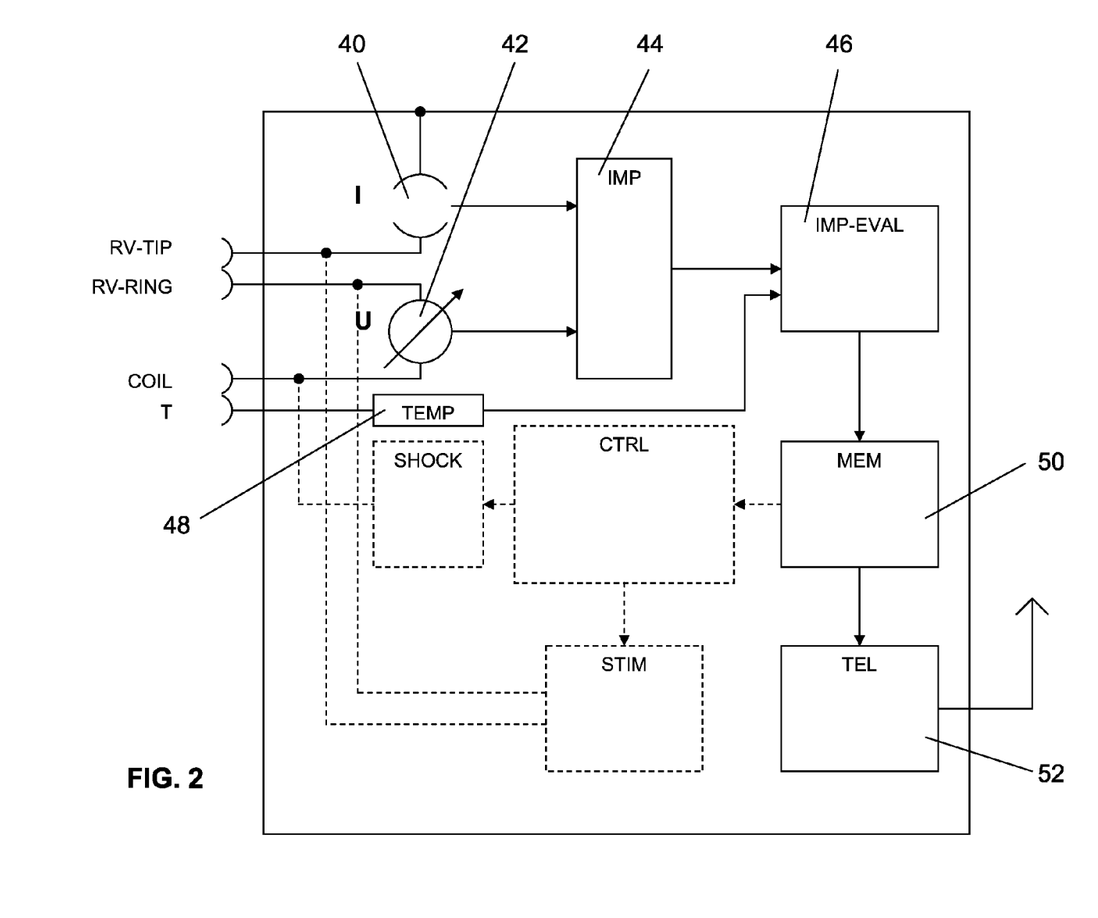
FIG. 2: shows a schematic block diagram of a first variant of a cardiac pacemaker/defibrillator according to the present invention.
Figure 3:
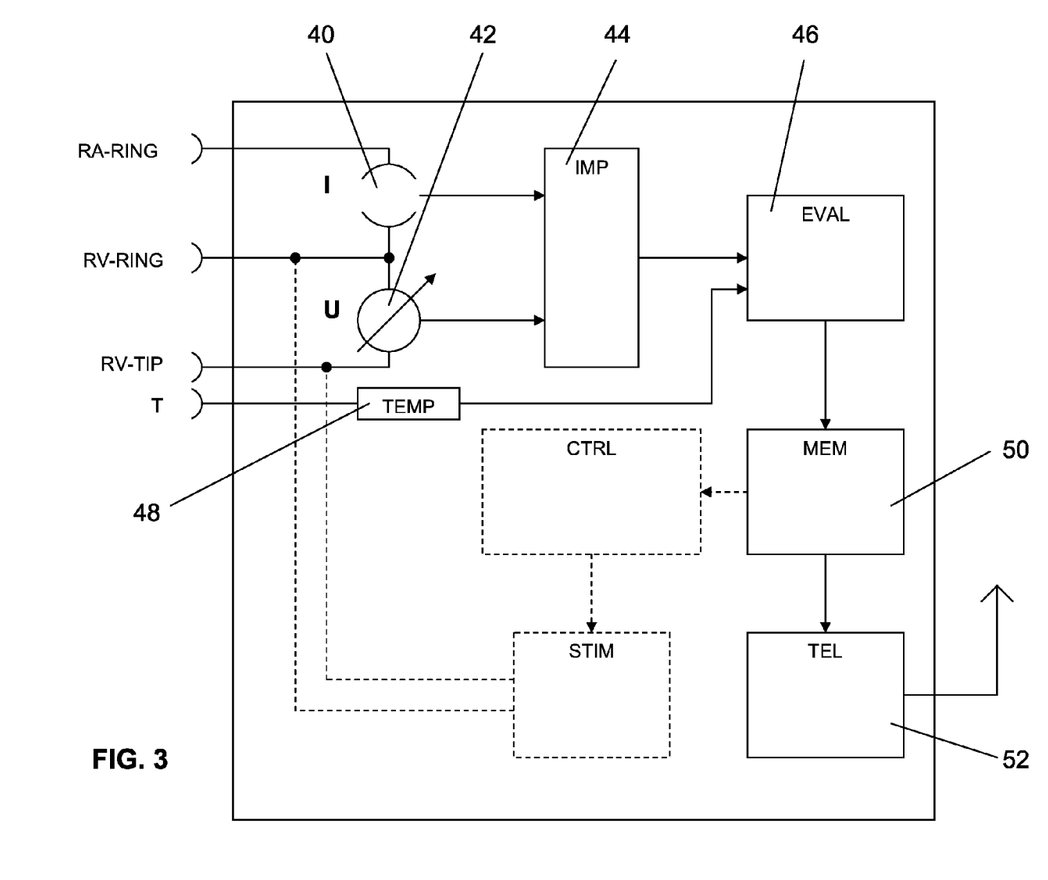
FIG. 3: shows a simplified block diagram of a second variant of the cardiac pacemaker/defibrillator according to the present invention.

FIGS. 2 and 3 schematically show some of the components situated in the interior of the housing 22 of the cardiac pacemaker and/or defibrillator 10 as examples. The typical components of an implantable cardiac pacemaker or defibrillator such as atrial and ventricular sensing stages, stimulation pulse generators, defibrillation shock generators, a control unit, etc. are not shown and/or are only partially indicated. These components and their variants are well-known to those skilled in the art.

An alternating current source 40, a voltage measuring unit 42, an impedance determination unit 44, and an impedance analysis unit 46 are particularly relevant in connection with the present invention. The alternating current source 40 is implemented for the purpose of generating a measuring current in the form of biphasic current pulses having constant current strength. The measuring current generated by the alternating current source 40 may have one of two alternating current frequencies below 100 kHz.

The alternating current source 40 is electrically connected in the configuration shown in FIG. 2 on one hand to the electrically conductive housing 22 of the cardiac pacemaker 10 and on the other hand to the terminal RV tip for a right-ventricular tip electrode.

The measuring unit 42 is connected in the configuration shown in FIG. 2 on one side to the terminal RV ring for a right-ventricular ring electrode and the terminal COIL for a shock coil and is implemented for the purpose of measuring the AC voltage caused between these two terminals as a result of the delivery of the measuring current by the alternating current source 40.

In the cardiac pacemaker 10 shown, the outputs of the alternating current source 40 and the inputs of the measuring unit 42 may be changed over and are connectable in this way to other available terminals. Various possible electrode configurations for the impedance or admittance measurement result therefrom. This is indicated by FIG. 3. Therein, the alternating current source 40 is connected on one side to a terminal for a right-atrial ring electrode and on the other side to the terminal for the right-ventricular ring electrode, while the measuring unit 42 is connected to the terminal for the right-ventricular ring electrode RV ring and the terminal RV tip for the right-ventricular tip electrode.

A switch which causes the differing connections of the outputs of the alternating current source 40 and the inputs of the measuring unit 42 is not shown in the figures. Fundamentally, however, the ability to change over the terminals of the alternating current source and the measuring unit may be provided between all electrodes shown in FIG. 1. Still further electrodes would be added in the case of biventricular implants or atrial defibrillators.

The alternating current source 40 and the measuring unit 42 are connected to the impedance determination unit 44, which calculates an impedance value from a particular delivered measuring current and the associated voltage detected by the measuring unit 42.

The impedance determination unit 44 is connected to the impedance analysis unit 46. The impedance analysis unit 46 is implemented for the purpose of calculating pairs of impedance values, the impedance values combined into pairs each being obtained at approximately identical times and using a measuring current of different frequency in each case. The impedance analysis unit 46 is also implemented to calculate a blood impedance component from these pairs of (total) impedance values, in that the impedance analysis unit 46 eliminates a tissue impedance component in the way described previously.

The impedance analysis unit 46 is also implemented to calculate an averaged impedance value pair over a quartile of all lowest impedance values within a predefined period of time or a predefined sequence of impedance values.

Finally, the impedance analysis unit 46 is connected to a temperature determination unit 48, which is in turn connected to a temperature sensor situated in proximity to the electrodes for the voltage measurement. In this way, the impedance analysis unit 46 is capable of considering changes of the blood temperature when analyzing the impedance values and isolating the component of a change of the blood impedance originating from a change of the hematocrit value.

As a result, the impedance analysis unit delivers an output value which is correlated to the blood impedance in such a way that changes of the output value of the impedance analysis unit reflect a change of the blood impedance as a result of a change of the hematocrit value, which is as free as possible from tissue impedances which are initially also measured, blood impedance changes as a result of temperature changes, or blood impedance changes as a result of electrode movements or movements of the vessels surrounding the electrodes. The output value of the impedance analysis unit is thus a function of the hematocrit value of the blood above all, so that changes of the output value of the impedance analysis unit 46 accompany changes of the hematocrit value of the blood and reflect them. Therefore, the output value of the impedance analysis unit 46 is useful in connection with the observation of a change of the hematocrit value of the blood of a patient.

The impedance determination unit 44 and the impedance analysis unit 46 together form an analysis unit which provides the output value described above.

This output value of the analysis unit, whose changes finally reflect changes of the hematocrit value of the blood of the patient, is fed to a memory 50, which is in turn connected to a telemetry unit 52. In this way, the output values of the impedance analysis unit 46 may be stored over a longer period of time for trend determination on one hand and may be transmitted to an external device for further analysis using the telemetry unit 52 on the other hand.

Further components of the cardiac pacemaker/defibrillator 10 such as a control unit, a shock pulse generator, or a stimulation pulse generator are only indicated in FIGS. 2 and 3.

What is claimed is:

1. An implantable medical device including:
   a. an impedance or admittance determination unit which is connected or is to be connected to electrodes to be placed intracardially or intraluminally for delivering a measuring current;
   b. an alternating current or AC voltage source which
      (1) generates
         (a) a measuring current as an alternating current of constant current amplitude, or
         (b) a measuring voltage as an AC voltage of constant voltage amplitude, and
      (2) feeds the measuring current or measuring voltage into the electrodes at different frequencies, the frequencies being below 500 kHz;
   c. a measuring unit which detects:
      (1) a voltage drop between two of the electrodes as a result of the fed measuring current, or
      (2) the current strength between two of the electrodes as a result of the fed measuring voltage;
   d. an analysis unit connected to the alternating current or AC voltage source and the measuring unit, wherein the analysis unit calculates:
      (1) pairs of impedance values or admittance values from:
         (a) the fed measuring current and the voltage drop detected as a result thereof, or
         (b) the fed measuring voltage and the current strength detected as a result thereof,
         each pair arising from different frequencies of the measuring current or measuring voltage;
      (2) a value for a blood impedance component or a blood admittance component which is at least substantially independent of the impedance or admittance of the body tissue surrounding a blood vessel from which the pairs of impedance values or admittance values are collected;
      (3) a relative change of the value of the blood impedance component or blood admittance component over time, the relative change serving as a measure of a change in blood hematocrit value.

2. The implantable medical device of claim 1 wherein the analysis unit calculates a tissue admittance a from the equation:

$$Y(f)=c*[(1-a)*\delta blood+a*\delta myocardium(f)]$$

wherein:
a. Y(f) is the sum of blood admittance and tissue admittance as a function of frequency f;
b. c is a constant,
c. $\delta$blood is the specific conductivity of blood,
d. $\delta$myocardium is the specific conductivity of body tissue.

3. The implantable medical device of claim 1 wherein the medical device measures the value for the blood impedance component or the blood admittance component using electrode configurations which change over time.

4. The implantable medical device of claim 1 wherein the analysis unit calculates pairs of impedance values from the fed measuring current and the voltage drop detected as a result thereof, each pair arising from different frequencies of the measuring current.

5. The implantable medical device of claim 4 wherein the analysis unit determines the relative change of the value of the blood impedance component over time using only pairs of impedance values which contain the lowest impedance values within:
   a. a predefined number of pairs of impedance values, or
   b. a predefined time window.

6. The implantable medical device of claim 1 further including a temperature determination unit connected to:
   a. a temperature sensor in communication with an electrode, and
   b. the analysis unit,
   wherein the analysis unit compensates for changes of blood temperature when determining the relative change of the value of the blood impedance or blood admittance component over time.

7. The implantable medical device of claim 1 wherein the alternating current source generates a measuring current as an alternating current of constant current amplitude in the form of biphasic current pulses.

8. The implantable medical device of claim 1 further including a memory storing one or more of:
   a. the blood impedance component over time,
   b. the blood admittance component over time, and
   c. the relative change of the value of the blood impedance component or blood admittance component over time.

9. The implantable medical device of claim 1 further including a telemetry unit which wirelessly transmits one or more of:
   a. the blood impedance component,
   b. the blood admittance component, and
   c. the relative change of the value of the blood impedance component or blood admittance component over time.

10. The implantable medical device of claim 1 wherein the device is one or more of:
    a. an implantable cardiac pacemaker, and
    b. an implantable cardioverter/defibrillator.

11. The implantable medical device of claim 1 wherein the analysis unit determines the amplitude of a circadian oscillation of one or more of:
    a. impedance values,
    b. admittance values,
    c. blood impedance component values, and
    d. blood admittance component values.

12. The implantable medical device of claim 11 wherein the analysis unit detects changes in the amplitude of the circadian oscillation, the changes serving as an indicator for a change of a hematocrit value of the blood.

13. An implantable medical device including:
    a. two or more electrodes,
    b. a power source supplying a measuring signal to the electrodes, the measuring signal being one or more of:
       (1) an alternating measuring current having constant current amplitude, and
       (2) an alternating measuring voltage having constant voltage amplitude,
       the measuring signal alternating at a signal frequency of approximately 500 kHz or less;
    c. a measuring unit which detects an inter-electrode signal, the inter-electrode signal being one or more of:
       (1) a voltage drop between the electrodes, and
       (2) a current strength between the electrodes,
       as a result of the measuring signal;
    d. an analysis unit connected to the power source and the measuring unit, wherein the analysis unit calculates one or more of:
       (1) impedance values, and
       (2) admittance values, from the measuring signal and the resulting inter-electrode signal at two or more different signal frequencies.

14. The implantable medical device of claim 13 wherein the analysis unit also calculates one or more of:
   a. a blood impedance component value, and
   b. a blood admittance component value,
   wherein the component value at least substantially reflects the impedance and/or admittance of a blood vessel wherein the electrodes are situated.

15. The implantable medical device of claim 14 wherein the analysis unit also calculates one or more of:
   a. change in the blood impedance component value over time, and
   b. change in the blood admittance component value over time,
   wherein the change provides a measure of the change in blood hematocrit value over time.

16. The implantable medical device of claim 13 further including a temperature sensor in communication with the analysis unit.

17. The implantable medical device of claim 16 wherein the temperature sensor is situated:
   a. on or within one or more of the electrodes, or
   b. on or within a lead extending from an electrode.

18. A method for measuring a change in blood hematocrit value including the steps of:
   a. supplying a measuring signal to two or more electrodes situated within a blood vessel, the measuring signal being one or more of:
      (1) an alternating measuring current having constant current amplitude, and
      (2) an alternating measuring voltage having constant voltage amplitude,
      the measuring signal alternating at a signal frequency of approximately 500 kHz or less;
   b. measuring an inter-electrode signal, the inter-electrode signal being one or more of:
      (1) a voltage drop between the electrodes, and
      (2) a current strength between the electrodes,
      as a result of the measuring signal;
   c. calculating one or more of:
      (1) impedance values, and
      (2) admittance values,
      from the measuring signal and the resulting inter-electrode signal at two or more different signal frequencies;
   d. calculating one or more of:
      (1) a blood impedance component value, and
      (2) a blood admittance component value,
      wherein the component value at least substantially reflects the impedance and/or admittance of the blood vessel wherein the electrodes are situated;
   e. calculating one or more of:
      (1) change in the blood impedance component value over time, and
      (2) change in the blood admittance component value over time,
      wherein the change in component value provides a measure of the change in blood hematocrit value over time.

19. The method of claim 18 wherein the calculation of the change in the component value uses the lowest impedance values and/or admittance values found within one or more of:
   a. a predefined number of impedance values and/or admittance values, and
   b. a predefined time window.

20. The method of claim 18 further including the steps of:
   a. measuring the temperature within or near the blood vessel, and
   b. adjusting the change in component value to compensate for temperature change.

21. An implantable medical device including:
   a. a power source configured to supply a pair of alternating electrical measuring signals to spaced electrodes situated in a blood vessel, the measuring signals:
      (1) being supplied to the electrodes simultaneously or in close succession, and
      (2) alternating at different signal frequencies;
   b. a measuring unit configured to detect a pair of inter-electrode signals, each inter-electrode signal including one or more of:
      (1) a voltage difference between the electrodes, and
      (2) a current strength between the electrodes,
      resulting from a corresponding one of the measuring signals;
   c. an analysis unit in communication with the power source and the measuring unit, the analysis unit being configured to calculate at least one of:
      (1) one or more of a blood impedance value and a blood admittance value, each value being at least substantially independent of the impedance or admittance of the body tissue surrounding the blood vessel, and
      (2) one or more of a tissue impedance value and a tissue admittance value, each value being at least substantially independent of the impedance or admittance of the blood adjacent the body tissue,
      from the measuring signals and their corresponding inter-electrode signals.

22. The implantable medical device of claim 21 wherein the analysis unit calculates one or more of the values in accordance with the relationship:

$$Y(f)=c*[(1-a)*\delta blood+a*\delta myocardium(f)]$$

wherein:
a. Y(f) is the sum of blood admittance and tissue admittance as a function of frequency f;
b. c is a constant,
c. a is a tissue admittance,
d. $\delta$blood is the specific conductivity of blood, and
e. $\delta$myocardium is the specific conductivity of body tissue.

23. The implantable medical device of claim 21 wherein:
a. the power source is configured to supply the measuring signals to, and
b. the measuring unit is configured to detect the inter-electrode signals from, different electrodes at different times.

* * * * *